US010352917B2

(12) United States Patent
Zhou et al.

(10) Patent No.: US 10,352,917 B2
(45) Date of Patent: Jul. 16, 2019

(54) CARBOXYLATE-BRIDGED BINUCLEAR IRON-SULFUR CLUSTERS FLUORESCENT PROBE, PREPARATION METHOD AND APPLICATION THEREOF

(71) Applicant: DALIAN UNIVERSITY OF TECHNOLOGY, Dalian, Liaoning (CN)

(72) Inventors: Yuhan Zhou, Liaoning (CN); Jingping Qu, Liaoning (CN); Xiaoliang Dong, Liaoning (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 156 days.

(21) Appl. No.: 15/410,426

(22) Filed: Jan. 19, 2017

(65) Prior Publication Data

US 2017/0131256 A1    May 11, 2017

Related U.S. Application Data

(63) Continuation-in-part of application No. PCT/CN2016/077950, filed on Apr. 1, 2016.

(30) Foreign Application Priority Data

Sep. 2, 2015   (CN) .......................... 2015 1 0561049

(51) Int. Cl.
*G01N 33/00*   (2006.01)
*G01N 33/18*   (2006.01)
(Continued)

(52) U.S. Cl.
CPC .......... *G01N 33/182* (2013.01); *C07F 15/02* (2013.01); *C07F 17/02* (2013.01); *C09B 1/00* (2013.01);
(Continued)

(58) Field of Classification Search
CPC .................................................... G01N 33/182
(Continued)

(56) References Cited

FOREIGN PATENT DOCUMENTS

| CN | 104788344 A | 7/2015 |
| CN | 105085581 A | 11/2015 |

OTHER PUBLICATIONS

Santos et al. (Supramolecular Chemistry, Jun. 2008 vol. 20 (4), pp. 407-418) (Year: 2008).*

(Continued)

*Primary Examiner* — Christine T Mui
*Assistant Examiner* — Emily R. Berkeley
(74) *Attorney, Agent, or Firm* — Novick, Kim & Lee, PLLC; Allen Xue (57) ABSTRACT

The present invention provides a carboxylate-bridged binuclear iron-sulfur clusters fluorescent probe having the structure of Formula I. The preparation method comprises the following steps: anthracenylmethanamine and p-methoxycarbonylphenyl isocyanate have an addition reaction to get a substitutional methyl benzoate, which is hydrolyzed to get a corresponding carboxylic acid; react the resulting carboxylic acid with alkali to get carboxylate, and then coordinate with binuclear iron precursor to obtain the fluorescent probe. Compared with the prior art, the invention firstly provides the carboxylate-bridged binuclear iron-sulfur clusters of metal complex which similar to the central structure of bio-enzyme. The metal complex, as a fluorescent probe, has good selectivity to the fluorinion detection. The fluorescence titration experiment is simple and easy to operate and the fluorescence changes are sensitive.

(Continued)

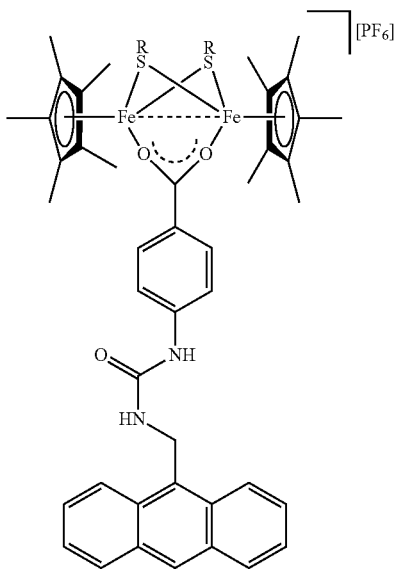

7 Claims, 6 Drawing Sheets (51) Int. Cl.
    *C07F 15/02* (2006.01)
    *C09K 11/06* (2006.01)
    *C09B 49/00* (2006.01)
    *G01N 21/64* (2006.01)
    *C07F 17/02* (2006.01)
    *C09B 1/00* (2006.01)

(52) U.S. Cl.
    CPC .............. *C09B 49/00* (2013.01); *C09K 11/06* (2013.01); *G01N 21/643* (2013.01); *C09K 2211/1007* (2013.01); *C09K 2211/1011* (2013.01); *C09K 2211/1014* (2013.01); *C09K 2211/187* (2013.01); *G01N 2021/6439* (2013.01)

(58) Field of Classification Search
    USPC .......................................................... 436/125
    See application file for complete search history.

(56) References Cited

OTHER PUBLICATIONS

Christine E. Tinberg et al., Dioxygen Activation in Soluble Methane Monooxygenase, Accounts of Chemical Research, Nov. 17, 2010, vol. 44, No. 4 pp. 280-288, American Chemical Society, Massachusetts 02139, United States.

Ane B. Tomter et al., Ribonucleotide reductase class I with different radical generating clusters, Coordination Chemistry Reviews, Jun. 23, 2012, pp. 3-26, Elsevier.

Ying Zhou et al., Fluorescence and Colorimetric Chemosensors for Fluoride-Ion Detection, Chemical Reviews, Mar. 25, 2014, 5511-5571, ACS Publications.

Philip A. Gale, Anion receptor chemistry: highlights from 2008 and 2009, Chemical Society Reviews, Jan. 27, 2010, pp. 3746-3771, DOI: 10.1039/c001871f, RSC publishing.

Jianwei Li et al., Study on optical recognition and electrochemical sensing of a 1,1'-ferrocenedicarbonylhydrazine derivative for fluoride, Applied Organometallic Chemistry, Feb. 6, 2008, pp. 258-261, DOI: 10.1002/aoc. 1387, John Wiley & Sons, Ltd.

Massimo Cametti et al., Recognition and sensing of fluoride anion, ChemComm journal, Apr. 9, 2009, pp. 2809-2829, DOI: 10.1039/b902069a, Royal Society of Chemistry.

Xue-Fang Shang et al., Anion recognition and sensing of ruthenium(II) and cobalt(II) sulfonamido complexes, Dalton Transactions, Jan. 30, 2009, pp. 2096-2102, DOI:10.1039/b804445g, Royal Society of Chemistry.

Tanaya Kundu et al., Selective recognition of fluoride and acetate by a newly designed ruthenium framework: experimental and theoretical investigations, Dalton Transactions, 2012, pp. 4484-4496, DOI: 10.1039/c2dt12126c, Royal Society of Chemistry.

Jia-Ming Liu et al., Zr(H2O)2 EDTA modulated luminescent carbon dots as fluorescent probes for fluoride detection, 2013, pp. 278-283, DOI: 10.1039/c2an36055a, Royal Society of Chemistry.

Chaolong Yang et al., An efficient long fluorescence lifetime polymer-based sensor based on europium complex as chromophore for the specific detection of F-, CH3COO-, and H2PO4-, 2012, pp. 2640-2648, DOI: 10.1039/c2py20408h, Royal Society of Chemistry.

Xiaoliang Dong et al., "Synthesis of carboxylate-bridged iron-thiolate clusters from alcohols/aldehydes or aarboxylate salts", Dalton Transactions, Jul. 13, 2015, vol. 44, pp. 14952-14958.

Yuhan Zhou et al., "Highly selective fluorescence sensors for the fluoride anion based on carboxylate-bridged diiron complexes", Dalton Transactions, 2016, vol. 45, pp. 6839-6846.

* cited by examiner

CARBOXYLATE-BRIDGED BINUCLEAR IRON-SULFUR CLUSTERS FLUORESCENT PROBE, PREPARATION METHOD AND APPLICATION THEREOF

TECHNICAL FIELD

The present invention relates to a carboxylate bridged binuclear iron-sulfur clusters fluorescent probe, preparation method and application thereof, which belongs to the iron detection in the fine chemical field.

BACKGROUND ART

There are many kinds of enzymes in the organism, including several bio-enzymes with central structure of carboxylate-bridged dinuclear iron, such as ribonucleotide reductase (RNR) and soluble methane monooxygenase (sMMO), which can catalyze some important substrates in the organisms and play a very important role. Therefore, it is a challenging work for simulating the structures and functions of these bio-enzymes and of great significance. (*Acc. Chem. Res.* 2011, 44, 280-288; *Coord. Chem. Rev.* 2013, 257, 3-26.).

Anions exist in the life body widely with very important functions. Fluoride ion is one of the trace elements indispensable to the human body. Fluorine is an indispensable part of the teeth and bones. Appropriate amount of fluoride ion can effectively prevent dental caries disease, so toothpastes contain a trace amount of fluoride ion. However, intake of a lot of fluoride ions may cause fluorosis, and diseases such as osteoporosis and urolithiasis, etc.; and if severe, it may affect children's intelligence development and physiological system. And domestic water contains a trace of fluoride ion. For its importance, the fluoride ion detection is particularly important and critical (*Chem. Rev.* 2014, 114, 5511-5571; *Chem. Soc. Rev.* 2010, 39, 3746-3771; *Chem. Commun.* 2009, 2809-2829.).

Methods for fluoride ion detection include electrochemical process, $^{19}$F-NMR analysis, UV analysis and fluorescence analysis. The first three methods have limitations such as expensive equipment, unable to have a real-time detection, etc., while the fluorescence analysis has the advantages of high sensitivity, real-time detection, ultra low concentration detection and intracellular detection, etc. Therefore fluorescence analysis for fluoride ion detection has attracted the attentions of researchers in recent years.

At present, the use of metal complex fluorescent probe to detect fluoride ion is rarely reported. The central metals of probes are mainly ruthenium (Ru), cobalt (Co), europium (Eu) and iron (Fe), etc., and most of the fluorophores or chromophores are phenanthroline and naphthalene, etc. (*Dalton Trans.* 2009, 12, 2096-2102; *Dalton Trans.* 2012, 41, 4484-4496; *Appl. Organometal. Chem.,* 2008, 22, 258-261; *Analyst,* 2013, 138, 278-283; *Polym. Chem.,* 2012, 3, 2640-2648.), while the fluoride ion fluorescent probes containing carboxylate-bridged binuclear iron-sulfur clusters have not been reported yet. Therefore, it has innovation and values to conduct studies on this type of fluoride fluorescent probes.

SUMMARY OF THE INVENTION

The present invention aims to provide a novel class of fluoride ion fluorescent probes containing carboxylate-bridged binuclear iron-sulfur clusters, which having the structure of formula I:

wherein, R is methyl or ethyl.

The invention also provides a method for preparing the carboxylate-bridged binuclear iron-sulfur clusters fluorescent probe, comprising the following steps:

(1) addition reaction: react anthracen-9-ylmethanamine with p-methoxycarbonylphenyl isocyanate at a temperature of 0-40° C. for 1-48 hours to get an addition product;

(2) hydrolysis reaction: react the addition product obtained in step (1) with alkaline aqueous solution at a temperature of 0-100° C. for 1-24 hours, then adjust pH to 6-7 with acidic aqueous solution to get a hydrolyzate;

(3) neutralization reaction: react the hydrolyzate obtained in step (2) with alkali at a temperature of 0-80° C. for 1-24 hours to get a ligand;

(4) coordination reaction: react the ligand obtained in step (3) with binuclear iron precursor at a temperature of 0-80° C. for 1-48 hours to get the fluorescent probe;

wherein the binuclear iron precursor is [Cp*Fe(μ-SR)$_2$(MeCN)$_2$FeCp*] [PF$_6$]$_2$; in which, Cp* is pentamethylcyclopentadienyl; R is Me(4a) or Et(4b).

For the preparation methods of the binuclear iron precursors 4a and 4b, refer to *J. Am. Chem. Soc.* 2011, 133, 1147-1149.

As a preferred technical solution, wherein at step (1), the molar ratio of anthracen-9-ylmethanamine to p-methoxycarbonylphenyl isocyanate is 1:1-2:1, and the reaction's solvent is at least one of dichloromethane, toluene, tetrahydrofuran, acetonitrile, ethyl acetate, acetone and ether.

As a preferred technical solution, wherein at step (2), the concentration of the alkaline aqueous solution is 1-5 mol/L, the ratio of the volume of alkaline aqueous solution to the mass of p-methoxycarbonylphenyl isocyanate is 5:1-50:1 mL/g.

As a preferred technical solution, wherein at step (3), the alkali is at least one of potassium t-butoxide, sodium t-butoxide, triethylamine, sodium hydride, sodium hydroxide, potassium hydroxide, sodium methoxide and sodium ethoxide; the molar ratio of the alkali to the hydrolyzate is 1:1-2:1.

As a preferred technical solution, wherein at step (4), the molar ratio of the added binuclear iron precursor to the ligand is 1:1-1:2; and solvent for the coordination reaction is at least one of dichloromethane, tetrahydrofuran, acetonitrile, and acetone.

Another object of the present invention is to provide an application for fluorinion detection of the aforesaid carboxylate-bridged binuclear iron-sulfur clusters fluorescent probe.

The fluorescent probes provided in the present invention can quickly and high-selectively realize fluorinion fluorescence enhancement detection.

Compared with prior arts, the present invention has advantages as follows:

(1) The present invention firstly provides a carboxylate-bridged binuclear iron-sulfur clusters of metal complex which similar to the central structure of bio-enzyme.

(2) The metal complex prepared in the present invention, as a fluorescent probe, has high-selectivity for fluorinion detection, simple and easy to operate the fluorescence titration experiment and the fluorescence changes sensitively.

BRIEF DESCRIPTION OF DRAWINGS

FIG. 5 shows the monocrystal structure of fluorescent probe 5a;

the bond length (Å), bond angle and dihedral angle (°) of 5a: Fe(1)-Fe(2) 2.5996(10), Fe(1)-S(1) 2.2031(15), Fe(1)-S(2) 2.2115(15), Fe(1)-O(1) 1.971(3), Fe(2)-S(1) 2.2025(16), Fe(2)-S(2) 2.2085(15), Fe(2)-O(2) 1.972(3), Fe(2)-S(1)-Fe(1) 53.83(4), Fe(2)-S(2)-Fe(1) 53.92(4), C(25)-O(2)-Fe(2) 122.7(3), C(25)-O(1)-Fe(1) 122.7(3), O(1)-Fe(1)-Fe(2) 84.85(10), O(1)-Fe(1)-S(2) 89.81(11), O(1)-Fe(1)-S(1) 90.57(11), O(2)-Fe(2)-Fe(1) 84.91(10), O(2)-Fe(2)-S(2) 89.7(1), S(1)-Fe(1)-S(2) 107.37 (6), Fe(2)-S(1)-Fe(1) 72.32 (5), Fe(2)-S(2)-Fe(1) 72.05(5), S(2)-Fe(1)-Fe(2) 53.92(4), S(2)-Fe(2)-Fe(1) 54.03(4), O(2)-C(25)-O(1) 124.7(4), Cp*(1)-Cp*(2) 55.94(15), S(1)Fe(2)Fe(1)-Fe(2)O(2)O(1)Fe(1) 86.7(7), O(2)C(25)O(1)-Fe(2)O(2)O(1)Fe(1) 4.4(4), C(34)C(35)C(40)C(41)C(42)C(47)-O(1)C(25)O(2) 70.3(4).

the bond length (Å), bond angle and dihedral angle (°) of 5b: Fe(1)-Fe(2) 2.6208(8), Fe(1)-S(1) 2.2067(13), Fe(1)-S(2) 2.2097(13), Fe(1)-O(1) 1.972(3), Fe(2)-S(1) 2.2008(12), Fe(2)-S(2) 2.1976(12), Fe(2)-O(2) 1.976(3), O(1)-C(25) 1.266(5), O(2)-C(25) 1.265(5), O(3)-C(32) 1.205(5), N(1)-C(32) 1.390(5), N(1)-C(29) 1.390(5), N(2)-C(32) 1.356(5), N(2)-C(33) 1.442(5), Fe(2)-S(1)-Fe(1) 72.39(4), Fe(2)-S(2)-Fe(1), C(25)-O(2)-Fe(2) 123.0(2), C(25)-O(1)-Fe(1) 122.7 (2), O(1)-Fe(1)-Fe(2) 84.97(8), O(1)-Fe(1)-S(2) 89.78(8), O(1)-Fe(1)-S(1) 90.17(8), O(2)-Fe(2)-Fe(1) 84.57(8), O(2)-Fe(2)-S(1) 89.52(9), O(2)-Fe(2)-S(2) 90.02(9), S(1)-Fe(1)-Fe(2) 53.70(3), S(1)-Fe(2)-Fe(1) 53.91(3), S(1)-Fe(1)-S(2) 106.96(5), Fe(2)-S(1)-Fe(1) 72.39(4), Fe(2)-S(2)-Fe(1) 72.40(4), S(2)-Fe(1)-Fe(2) 53.59(3), S(2)-Fe(2)-Fe(1) 54.02 (3), O(2)-C(25)-O(1) 124.8(3), Cp*(1)-Cp*(2) 54.03(12), S(1)Fe(2)Fe(1)-Fe(2)O(2)O(1)Fe(1) 90.0(7), O(2)C(25)O(1)-Fe(2)O(2)O(1)Fe(1) 1.2(4). C(34)C(35)C(40)C(41)C(42)C(47)-O(1)C(25)O(2) 84.91(3).

DETAILED DESCRIPTIONS OF THE PREFERRED EMBODIMENTS

The present invention is described in combination with embodiments in details, but the following embodiments are only preferred modes of execution without limiting the present invention in any way. Those person skilled in the art can make equivalent replacements or changes to the present invention, which according to the technical solutions and inventive concepts within the disclosed technical scope of the present invention, shall fall into the protection scope of the present invention.

The reaction mechanism of the preparation method of carboxylate-bridged binuclear iron-sulfur clusters fluorescent probe is as follows:

(1) addition reaction react anthracen-9-ylmethanamine with p-methoxycarbonylphenyl isocyanate to get a corresponding carboxylic ester;

(2) hydrolysis reaction react the product solution obtained in step (1) with alkaline aqueous solution to obtain an hydrolyzate 3;

(3) neutralization reaction react the hydrolyzate 3 obtained in step (2) with alkali to get a carboxylate;

(4) coordination reaction react the carboxylate obtained in step (3) with binuclear iron precursor 4a or 4b to get fluorescent probes 5a or 5b.

Embodiment 1 Synthesis of Carboxylate-Bridged Binuclear Iron-Sulfur Clusters Fluorescent Probe 5a To a solution of anthracen-9-ylmethanamine (1 g) in $CH_2Cl_2$ (180 mL) was added p-methoxycarbonylphenyl isocyanate (0.86 g) and then the resulting solution was stirred at room temperature for 24 h. The mixture was filtered to get filter cake and washed with $CHCl_3$ to give solid. To a solution of the solid in EtOH (10 mL) was added NaOH solution (2 M, 10 mL) and the resulting solution was stirred at 75° C. for 12 h. After being adjusted to pH=6 with diluted hydrochloric acid (3 M), the solution was filtered and washed with $H_2O$ (5 mL) and EtOH (5 mL) to give crude solid. The solid was crystallized from DMSO-acetone to give hydrolyzate 3 (0.92 g, 52%).

$^1$H NMR (400 MHz, DMSO-d$^6$): δ11.24 (br, 1H), 8.99 (s, 1H), 8.61 (br, 1H), 8.54 (d, $J_{H-H}$=8 Hz, 2H), 8.11 (br, 2H), 7.72 (br, 2H), 7.54-7.61 (m, 4H), 7.35 (br, 3H), 5.31 (br, 2H). $^{13}$C NMR (100 MHz, DMSO-D$^6$): δ155.08, 141.50, 131.08, 130.97, 129.78, 128.83, 127.11, 126.22, 125.17, 124.60, 115.93, 35.17.

ESI-HRMS (m/z): [M-H]$^-$ 369.1317; calcd. value for $C_{23}H_{18}N_2O_3$: 369.1326.

To a solution of hydrolyzate 3 (72 mg) in THF (30 mL) was added t-BuOK (22 mg) and then the resulting solution was reacted at 50° C. for 2 h. After the solution was removed in vacuum, $CH_3CN$ (30 mL) and binuclear iron precursor 4a (150 mg) were added. The resulting solution was allowed to react for 48 h at room temperature under argon, the solution was filtered, and $CH_3CN$ was removed in vacuum. Then, the residue was extracted with $CH_2Cl_2$ (3 mL). After filtration and removal of the $CH_2Cl_2$ in vacuum, the residue was extracted with THF (3 mL). After filtration and removal of the THF, the residue was washed with $Et_2O$ (2 mL×2) to give light green solid 5a ((108 mg, 60%).

$^1$H NMR (400 MHz, CD$_2$Cl$_2$): δ8.43 (s, 1H), 8.32 (br, 2H), 7.99 (br, 2H), 7.44-7.50 (m, 4H), 7.13 (br, 2H), 6.95 (br, 2H), 6.72 (s, 1H), 5.25 (br, 2H), 1.79 (s, 6H), 1.43 (s, 30H). IR (KBr, cm$^{-1}$): 3419 (m), 2921 (s), 1695 (m), 1597 (m), 1550 (m), 1516 (s), 1397 (s), 1375 (m), 1318 (m), 1216 (w), 1178 (m), 1018 (m), 955 (w), 842 (s), 778 (m), 735 (m).

ESI-HRMS (m/z): [M-PF$_6$]$^+$ 845.2170; calcd. value for $C_{45}H_{53}Fe_2N_2O_3S_2$: 845.2196.

Embodiment 2 Synthesis of Carboxylate-Bridged Binuclear Iron-Sulfur Clusters Fluorescent Probe 5b 4b was used as the binuclear precursor, and the other procedures were the same as those in Embodiment 1, to get 5b (105 mg, 58%).

$^1$H NMR (400 MHz, CD$_2$Cl$_2$): δ8.44 (s, 1H), 8.33 (d, =8 Hz, 2H), 8.01 (d, $J_{H-H}$=8 Hz, 2H), 7.46-7.51 (m, 4H), 7.14 (d, $J_{H-H}$=8 Hz, 2H), 6.93 (d, $J_{H-H}$=8 Hz, 2H), 6.73 (s, 1H), 5.33 (br, 2H), 5.26 (br, 1H), 1.93 (t, =8 Hz, 6H), 1.63 (q, $J_{H-H}$=8 Hz, 4H), 1.46 (s, 30H). IR (KBr, cm$^{-1}$): 3421 (m), 3056 (w), 2981 (m), 2925 (s), 1698 (s), 1597 (s), 1519 (s), 1448 (w) 1403 (s), 1375 (m), 1319 (m), 1231 (m), 1178 (m), 1073 (w), 1018 (s), 845 (s), 778 (m), 736 (m).

ESI-HRMS (m/z): [M-PF$_6$]$^+$ 873.2506; calcd. value for $C_{47}H_{57}Fe_2N_2O_3S_2$: 873.2509.

Figure 1:
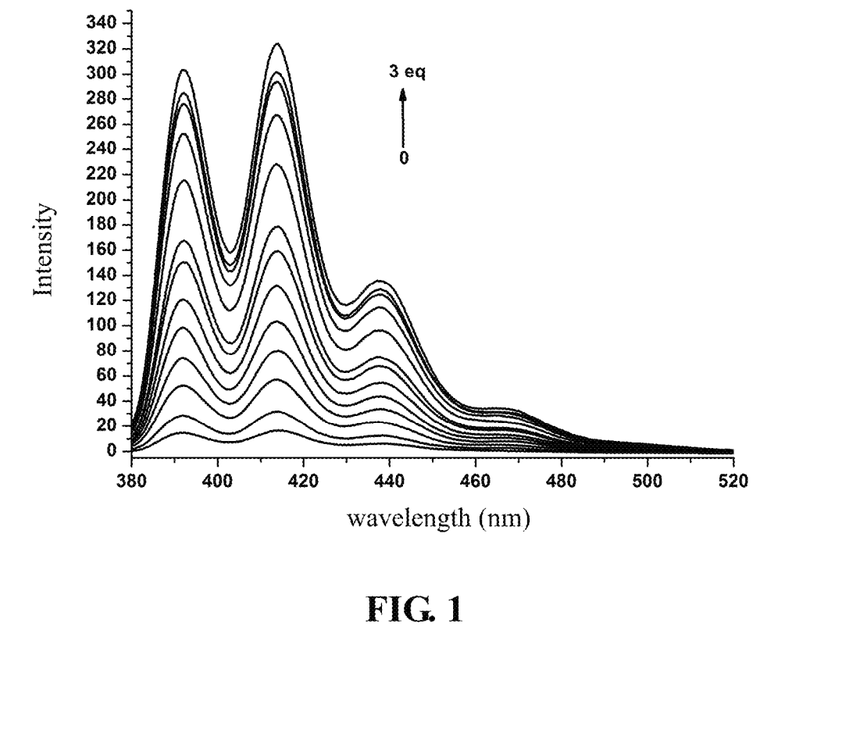
FIG. 1 shows the fluorescence spectra of fluorescent probe 5a reacts with different amount of $F^-$.

Embodiment 3 The Effect of the Amount of Fluoride Ion on the Fluorescent Probe 5a Fluorescent Emission 3 mL of $10^{-5}$ mol/L 5a (prepared as described in embodiment 1) tetrahydrofuran solution was taken each time to a cuvette, then 0.2 eq, 0.4 eq, 0.6 eq, 0.8 eq, 1.0 eq, 1.2 eq, 1.4 eq, 1.6 eq, 1.8 eq, 2.0 eq, 2.2 eq, 2.4 eq, 2.6 eq, 2.8 eq and 3.0 eq of tetrabutylammonium fluoride aqueous solutions were added ordinally to test their fluorescence emission spectra, and get the results as shown in FIG. 1. It can be seen from this figure, with the increase of the fluoride ions, the fluorescence of the system was significantly enhanced.

Figure 2:
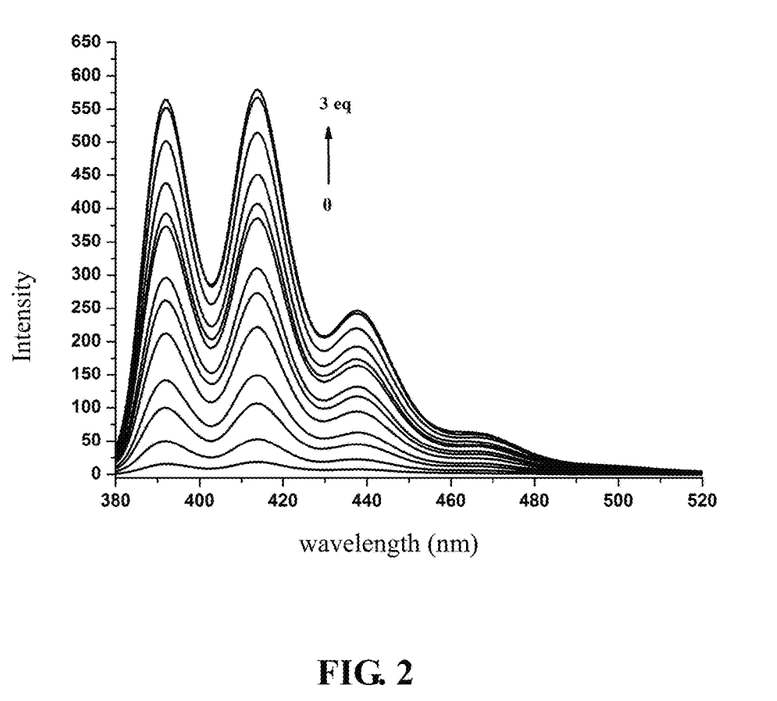
FIG. 2 shows the fluorescence spectra of fluorescent probe 5b reacts with different amount of $F^-$.

The effect of the amount of fluoride ion on the fluorescent probe 5b fluorescence emission can be obtained by the same way, as shown in FIG. 2.

Figure 3:
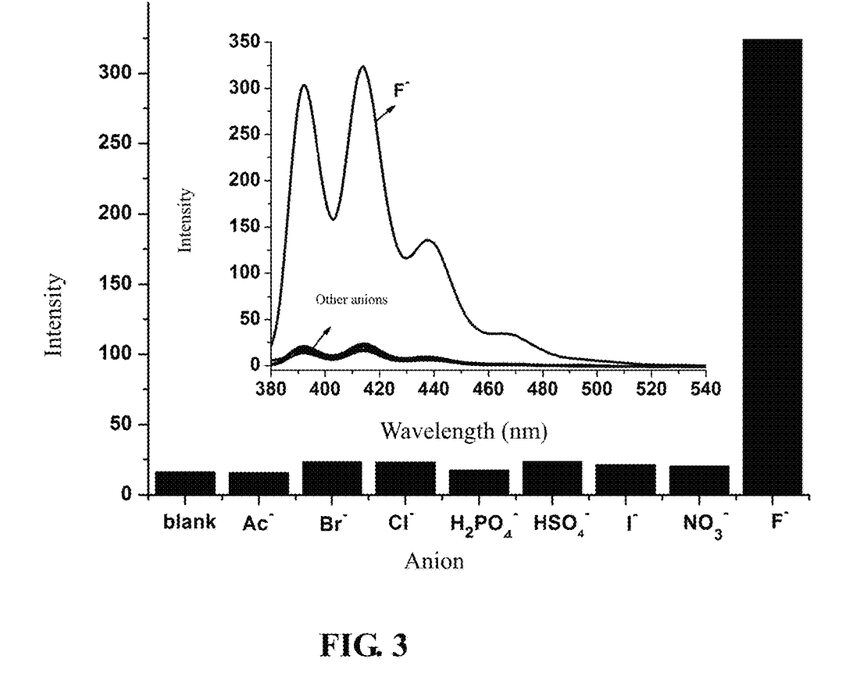
FIG. 3 shows the fluorescence spectra of fluorescent probe 5a reacts with different anions.

Embodiment 4 The Effect of Different Anions on the Fluorescent Probe 5a Fluorescent Emission 3 mL of $10^{-5}$ mol/L 5a (prepared as described in embodiment 1) tetrahydrofuran solution was taken each time to a cuvette, then 3 eq of $F^-$, $Br^-$, $H_2PO_4^-$, $HSO_4^-$, $Ac^-$, $NO_3^-$ and $I^-$ were added ordinally, and under the effect of 370 nm exciting light to test the fluorescence emission spectra, and get the results as shown in FIG. 3. As can be seen from this figure, the system could selectively identify fluorinion.

Figure 4:
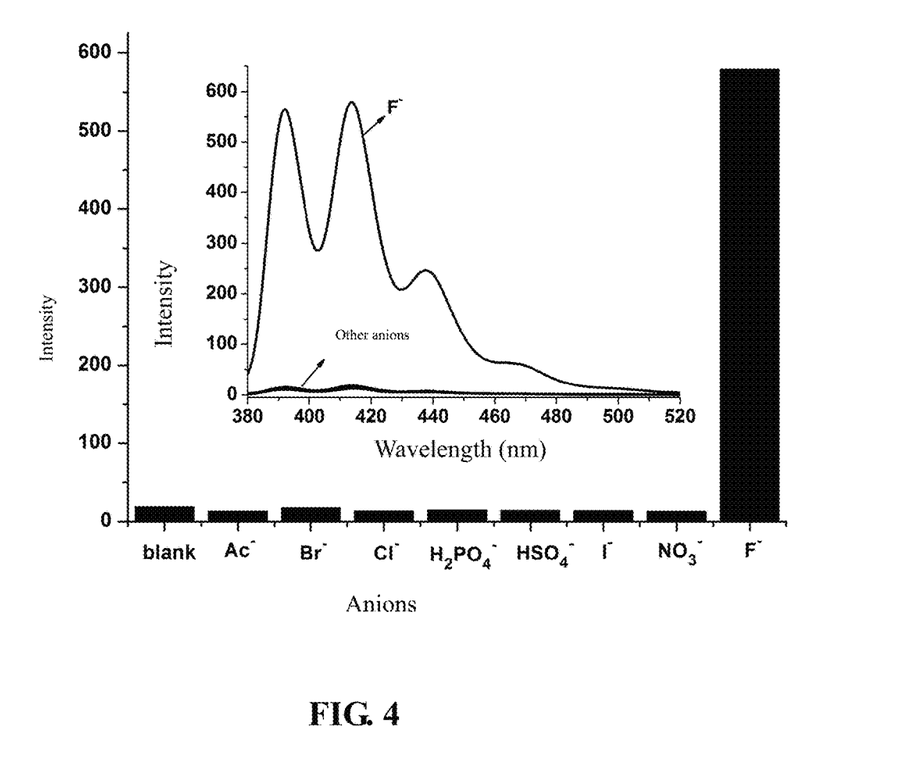
FIG. 4 shows the fluorescence spectra of fluorescent probe 5b reacts with different anions.
Figure 5:
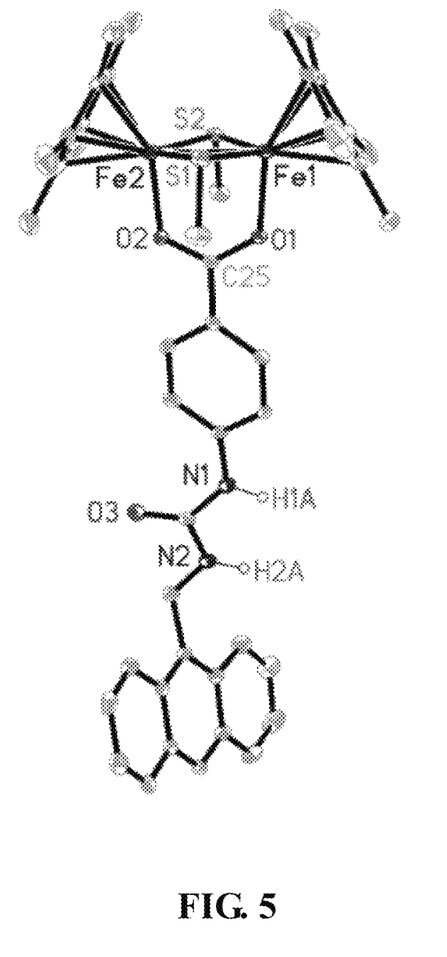
Figure 6:
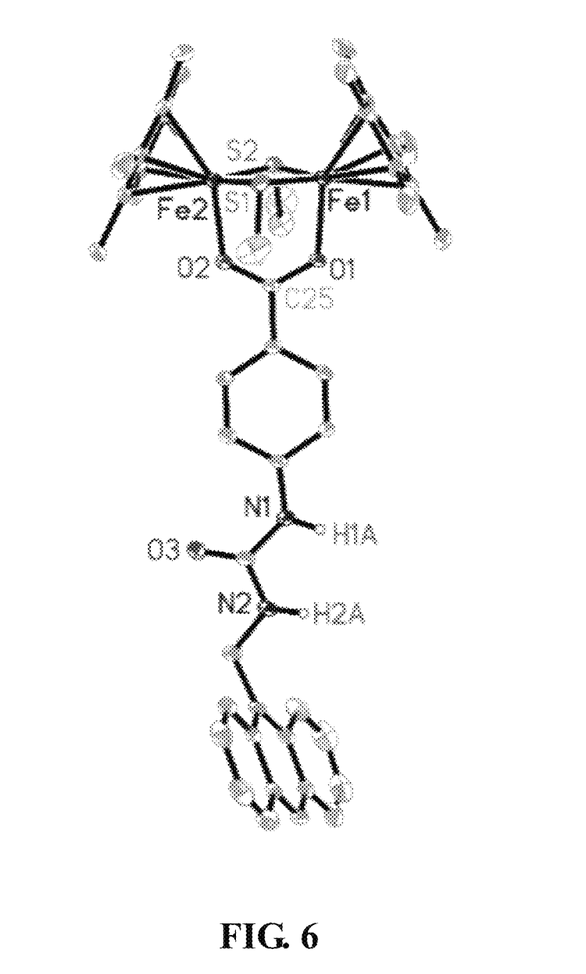
FIG. 6 shows the monocrystal structure of fluorescent probe 5b.

The effect of different anions on the fluorescent probe 5b fluorescent emission could be obtained by the same way, as shown in FIG. 4.

The invention claimed is:

1. Carboxylate-bridged binuclear iron-sulfur clusters fluorescent probe of formula I, wherein R is methyl or ethyl.

2. A preparation method of the carboxylate-bridged binuclear iron-sulfur clusters fluorescent probe according to claim 1, comprising:
   (1) reacting anthracen-9-ylmethanamine with p-methoxycarbonylphenyl isocyanate in a first solvent at a temperature of 0-40° C. for 1-48 hours to obtain an addition product;
   (2) reacting the addition product obtained in step (1) with an alkaline aqueous solution at a temperature of 0-100° C. for 1-24 hours, then adjusting pH to 6-7 with acidic aqueous solution to obtain an hydrolyzate;
   (3) reacting the hydrolyzate obtained in step (2) with alkali at a temperature of 0-80° C. for 1-24 hours to obtain a ligand; and
   (4) reacting the ligand obtained in step (3) with a binuclear iron precursor in a second solvent at a temperature of 0-80° C. for 1-48 hours,
   wherein the binuclear iron precursor is $[Cp^*Fe(\mu\text{-}SR)_2(MeCN)_2FeCp^*][PF_6]_2$, $Cp^*$ is pentamethylcyclopentadienyl, and R is Me or Et.

3. The preparation method of the carboxylate-bridged binuclear iron-sulfur clusters fluorescent probe according to claim 2, wherein in step (1), a molar ratio of anthracen-9-ylmethanamine to p-methoxycarbonylphenyl isocyanate is 1:1 to 2:1, and the first solvent is selected from the group consisting of dichloromethane, toluene, tetrahydrofuran, acetonitrile, ethyl acetate, acetone, ether, and mixtures thereof.

4. The preparation method of the carboxylate-bridged binuclear iron-sulfur clusters fluorescent probe according to claim 2, wherein in step (2), the alkaline aqueous solution has a concentration of 1-5 mol/L, and a ratio of the volume of alkaline aqueous solution to the mass of p-methoxycarbonylphenyl isocyanate is 5:1 to 50:1 mL/g.

5. The preparation method of the carboxylate-bridged binuclear iron-sulfur clusters fluorescent probe according to claim 2, wherein, in step (3), the alkali is selected from the group consisting of potassium t-butoxide, sodium t-butoxide, triethylamine, sodium hydride, sodium hydroxide, potassium hydroxide, sodium methoxide, sodium ethoxide, and mixtures thereof, and a molar ratio of the alkali to the hydrolyzate is 1:1 to 2:1.

6. The preparation method of the carboxylate-bridged binuclear iron-sulfur clusters fluorescent probe according to claim 2, wherein, in step (4), a molar ratio of the added binuclear iron precursor to the ligand is 1:1 to 1:2; and the second solvent is selected from the group consisting of dichloromethane, tetrahydrofuran, acetonitrile, acetone, and mixtures thereof.

7. A method for detecting fluorine ions, comprising:
   forming a mixture comprising the carboxylate-bridged binuclear iron-sulfur clusters fluorescent probe according to claim 1 and fluorine ions;
   shining an excitation light on the mixture; and
   recording a fluorescent light emitting from the mixture.

* * * * *